United States Patent [19]

Burzin et al.

[11] 4,136,098
[45] Jan. 23, 1979

[54] PROCESS FOR THE PRODUCTION OF CYCLIC ESTERS OF UNDECANEDIOIC ACID

[75] Inventors: Klaus Burzin; Jörn Rüter, both of Marl, Fed. Rep. of Germany

[73] Assignee: Chemische Werke Huels, A.G., Marl, Fed. Rep. of Germany

[21] Appl. No.: 881,932

[22] Filed: Feb. 28, 1978

[30] Foreign Application Priority Data

Apr. 1, 1977 [DE] Fed. Rep. of Germany ....... 2714564

[51] Int. Cl.$^2$ ........................................... C07D 321/00
[52] U.S. Cl. .................................................... 260/343
[58] Field of Search ......................................... 260/343

[56] References Cited

U.S. PATENT DOCUMENTS

| 2,020,298 | 11/1935 | Carothers et al. | 260/343 |
| 2,936,310 | 5/1960 | Beets et al. | 260/343 |

FOREIGN PATENT DOCUMENTS

| 796410 | 10/1935 | France | 260/343 |
| 1474903 | 1966 | France | 260/343 |
| 1528546 | 6/1968 | France | 260/343 |
| 47-25071 | 7/1972 | Japan | 260/343 |

OTHER PUBLICATIONS

Hill et al., Jour. American Chemical Soc., 55, 5031–5039, 1933.
Yasukawa et al., Chem. Abstracts, vol. 78, 1973, 158966q and 158968s.

Primary Examiner—Natalie Trousof
Assistant Examiner—Jane T. Fan
Attorney, Agent, or Firm—Millen & White

[57] ABSTRACT

A process for the production of cyclic esters of undecanedioic acid with aliphatic diols comprising thermolyzing the corresponding linear polyesters derived from said acid and said diols under reduced pressure at temperatures of 200°–300° C in the presence of organotin and phosphonate catalysts, wherein the organotin catalyst is of the formula

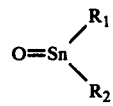

wherein $R_1$ and $R_2$ are alkyl of 1–18 carbon atoms, or aryl or aralkyl each of 6–36 carbon atoms, and the phosphonate is O,O-dialkyl-(3,5-di-tert-butyl-4-hydroxybenzyl)-phosphonate, the alkyl groups of which each contain 2–18 carbon atoms.

13 Claims, No Drawings

PROCESS FOR THE PRODUCTION OF CYCLIC ESTERS OF UNDECANEDIOIC ACID

BACKGROUND OF THE INVENTION

The production of a cyclic diester from undecanedioic acid and ethylene glycol by depolymerization of the corresponding polyester composed of the acid and the glycol in the absence of a catalyst has been described by Carothers and Hill [J. Amer. Chem. Soc. 55, 5,031–5,039 (1933)]. In this process, cyclo(ethyleneundecanedioate) is obtained in trace amounts only. The cyclic dimer is formed as the primary reaction product.

The preparation of cyclic diesters by the thermolysis of linear polyesters in the presence of inorganic salts, such as the chlorides, nitrates, carbonates, or oxides of magnesium, manganese, iron, cobalt, or tin as the catalysts has been described in French Pat. No. 796,410. This reference contains no disclosure concerning the production of cyclic diesters of undecanedioic acid. If an attempt is made to produce cyclic diesters of undecanedioic acid according to this process, yields of merely less than 15% are attained.

Better yields can be achieved according to the processes described in Japanese Laid-Open Applications Nos. 4,826,790 and 4,920,503, wherein linear polyesters of aliphatic dicarboxylic acids and diols are treated at temperatures of 260°–280° C. under reduced pressure with lead nitrate and/or lead dioxide. Examples with undecanedioic acid are not disclosed in either reference. Both processes have the disadvantage that lead compounds must be used as the catalysts, the use of which is increasingly being restricted due to the notorious toxicity of lead compounds. Even worse, the cyclic diesters produced according to these methods themselves contain quite considerable quantities of lead. Since the cyclic diesters are utilized primarily in the cosmetics industry as fixing agents in perfumes, soaps, or mouthwashes (see DOS [German Unexamined Laid-Open Application] No. 2,440,526), the use of such lead compounds is prohibited. Even the elimination of the lead-containing residue from the thermolysis product is problematic because of the attendant environmental hazards due to, inter alia, lead-containing waste air emanating during the combustion of the residue, as well as poisoning of the wastewater and/or ground water if the residues are dumped.

A general disadvantage of all heretofore described processes for the production of cyclic diesters by the catalytic depolymerization of the corresponding polyesters resides in the rapid rise in viscosity which takes place in the reaction charge. This occurs even at the beginning of the splitting-off reaction undergone by the cyclic diester. It continues until crosslinking occurs, which makes it impossible to agitate the reaction batch after about only 10–15% of the cyclic diester has been split off, based on the amount of polyester employed, as can be seen from Comparative Examples 10–18 herein. For this reason, the heretofore described processes operate without any agitation of the thermolysis batch. This, however, is possible only when the polyester is thermolyzed on a laboratory scale, i.e., using only 50–100 g per batch. In order to depolymerize larger amounts of polyester in larger devices, it is absolutely necessary to agitate the reaction charge in order to provide sufficient heat transfer. Furthermore, the removal of the crosslinked residue of the thermolysis entails great difficulties in industrial batches. Thus, it is quite apparent that the aforementioned processes are entirely unsuitable for the production of the cyclic diesters in large quantities.

As a result, Japanese Application Sho-48/111 299 suggested a process for the production of cyclic esters by the depolymerization of linear polyesters under reduced pressure in the presence of dialkyl lead or tin oxides and an azeotropic agent. The azeotropic agent (paraffin oil), which is simultaneously also used to prevent a rise in melt viscosity during the thermolysis, is removed during the depolymerization together with the cyclic diester by azeotropic distillation. The cyclic diester is isolated from the resultant mixture by extraction and then purified by distillation.

It is clearly apparent that this process, as compared to the mere thermolysis, comprises several additional operating steps. Most significantly, difficulties are encountered in the purification of the cyclic ester because the azeotropic agent has a similar boiling point, and/or the procedure requires great technical expenditures.

SUMMARY OF THE INVENTION

Accordingly, it is an object of the present invention to provide a process for the production of cyclic diesters of undecanedioic acid which enables the manufacture of the esters in large batches, in high yields, and free of toxic compounds and large amounts of hard to remove azeotropic agents.

Upon further study of the specification and appended claims, further objects and advantages of this invention will become apparent to those skilled in the art.

These objects have been achieved by providing a process for the production of cyclic esters of undecanedioic acid with aliphatic diols which comprises thermolyzing the corresponding linear polyesters derived from said acid and said diols under reduced pressure at temperatures of 200°–300° C. in the presence of organotin and phosphonate catalysts, wherein the organotin catalyst is of the formula

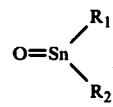

wherein $R_1$ and $R_2$ are alkyl of 1–18 carbon atoms, or aryl or aralkyl each of 6–36 carbon atoms, and the phosphonate is O,O-dialkyl-(3,5-di-tert-butyl-4-hydroxybenzyl)-phosphonate, the alkyl groups of which each contain 2–18 carbon atoms.

DETAILED DISCUSSION

The linear polyesters of undecanedioic acid utilized as starting material can be produced according to methods well known to those skilled in the art. They are described, for example, by Korshak and Vinogradova in *Polyesters*, pp. 153 et seq. (Permagon Press, 1965). Some of these linear polyesters are also available commercially.

To prevent the formation of an excessive amount of by-products during the thermolysis, the linear polyester should be of maximum purity. It is furthermore advantageous to utilize polyesters wherein the acid number is lower than about 10 mg KOH/g, preferably from 0–8 mg KOH/g, to avoid secondary reactions of carboxyl end groups as much as possible. The mean degree of polymerization should be about 3–200, preferably about 10–50, since polyesters of this degree of polymerization show a readily controllable melt viscosity.

Primarily suited as the diol component are aliphatic straight-chain diols which contain 2–12 carbon atoms, preferably 2–4 carbon atoms in the chain. The diols can additionally be substituted with up to 2 alkyl groups of up to 4 carbon atoms each. Especially advantageous diols include ethylene glycol, 1,2-propanediol, 1,3-propanediol, 1,4-butanediol, 1,6-hexanediol, 1,12-dodecanediol, 2,2-dimethyl-1,3-propanediol, 3,3-dimethyl-1,5-pentanediol, 2,2-diethyl-1,3-propanediol, and 2-n-butyl-2-ethyl-1,3-propanediol.

The organotin compounds of this invention, which act catalytically together with O,O-dialkyl-(3,5-di-tert-butyl-4-hydroxybenzyl)-phosphonate, have the following formula

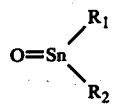

$R_1$ and $R_2$ each are alkyl groups of 1–18 carbon atoms, preferably 4–12 C-atoms, e.g., methyl, ethyl, propyl, butyl, isobutyl, pentyl, hexyl, octyl, nonyl, dodecyl, pentadecyl or octadecyl; or aryl or aralkyl groups of 6–36 total carbon atoms, preferably 6–18 C-atoms, for example phenyl, benzyl, naphthyl or toluyl. The following organotin compounds are preferably employed: dipropyltin oxide, dibutyltin oxide, dihexyltin oxide, dioctyltin oxide, didodecyl(dilauryl)tin oxide, dipentadecyltin oxide, dioctadecyl(distearyl)tin oxide, diphenyltin oxide, and dibenzyltin oxide, especially dioctyltin oxide, didodecyltin oxide, dipentadecyltin oxide, dioctadecyltin oxide, diphenyltin oxide, and dibenzyltin oxide. The special advantage of these dialkyl tin oxides is derived from the fact that none or only trace amounts of them pass into the product of the thermolysis. This is due to their low vapor pressure. As a result, they need not be removed from the product by additional, special purification operations. Such compounds are described, for example, in Fortschr. Chem. Forsch. (Topics in current chemistry) 16, 365–403 (1970).

The O,O-dialkyl-(3,5-di-tert-butyl-4-hydroxybenzyl)-phosphonate to be utilized together with the organotin compound contains 2–18 carbon atoms in each alkyl group. Especially suitable is O,O-dioctadecyl-(3,5-di-tert-butyl-4-hydroxybenzyl)-phosphonate. Such compounds are readily preparable and also available commercially. They are described, for example, in U.S. Pat. Nos. 3,281,505 and 3,367,870.

The amounts of organotin compound and of O,O-dialkyl-(3,5-di-tert-butyl-4-hydroxybenzyl)-phosphonate to be employed are each about 0.1–5% by weight, based on the amount of polyester employed. At below 0.1% by weight for each, the desirable catalytic effects become increasingly smaller, and above 5% by weight for each, the effects no longer increase. The addition of amounts of either above 5% by weight is possible without any disadvantages, but does not serve any useful purpose. Good results are attained with additions of about 1% and 3% by weight for each catalytic component. In a preferred mode, equal amounts of each component are employed.

The catalyst components are generally mixed with the linear polyester prior to the thermolysis. Thereafter, the mixture is transferred into the reactor and thermolyzed under agitation and reduced pressure. It is, however, likewise possible to mix the linear polyester with the catalysts after either has first been charged into the reactor. The order of addition of the three components is not critical.

The temperature required for the thermolysis is 200–300° C. At below 200° C., the thermolysis proceeds too slowly; at above 300° C., undesired cracking reactions occur. Temperatures of 250–280° C. are especially advantageous. In this range, the cyclic diesters are split-off at a lively pace without the premature occurrence of undesired cracking reactions.

To remove the reaction product at maximum speed from the reaction zone, thus preventing the product from entering into secondary reactions, the thermolysis is conducted under reduced pressure. Suitably, the pressure is selected so that it is equal or lower than the vapor pressure of the reaction product at the reaction temperature employed. Thus, the reaction product is immediately removed from the reaction mixture by distillation. The reaction takes place particularly smoothly at pressures below 1 mbar. Suitable pressures are below 5 mbar, preferably below 1 mbar. The removal of the reaction product from the reaction zone can also be enhanced by the introduction of an inert carrier gas stream (e.g., nitrogen). Typical flow rates are 2–10 l/min.

In a discontinuous mode of operation (batch), the thermolysis is continued until the reaction charge can no longer be stirred. Typical reaction times are 4–12 hours, preferably 5–8 hours. However, the process can also be carried out continuously, for example, in a thin-film evaporator or a vacuum extruder, in which case typical residence times are 5–30 min.

In the process of this invention, the cyclic diester products are obtained as colorless to slightly yellow-colored substances which, if necessary, can subsequently be subjected to a fine purification step such as vacuum distillation or recrystallization.

The advantages attainable by this invention reside, above all, in the facts that a reaction product can be produced in high yields, free of toxic residues and independent from large quantities of azeotropic agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degress Celsius; unless otherwise indicated, all parts and percentages are by weight.

EXAMPLE 1

100 g of a polyester of undecanedioic acid and ethylene glycol, having an average degree of polymerization of 33 and an acid number of 5 mg KOH/g, is intimately mixed with 3 g of dioctyltin oxide and 3 g of O,O-dioctadecyl-(3,5-di-tert-butyl-4-hydroxybenzyl)-phosphonate in a distillation flask of a conventional vaccum distillation apparatus. The mixture is heated to 270° C. under a vacuum of below 1 mbar. While the polyester is foaming, cyclo(ethyleneundecanedioate) is distilled. The thermolysis is terminated after 4–6 hours. The crude yield of 1,4-dioxacyclopentadecane-5,15-dione is 64%, based on the amount of polyester employed. For purifying purposes, the product is recrystallized from methanol.

Pure yield: 61%; m.p. 38° C.

EXAMPLE 2

100 g of a polyester of undecanedioic acid and 1,3-propanediol, having a degree of polymerization of 29 and an acid number of 7 mg KOH/g, is thoroughly mixed with 3 g of dioctyltin oxide and 3 g of O,O-dioctadecyl-(3,5-di-tert-butyl-4-hydroxybenzyl)-phosphonate in a distillation flask of a conventional vacuum distillation apparatus. The reaction mixture is thermolyzed for 4 hours under vacuum (pressure: 0.2 mbar) and at a temperature of 270° C. The yield of crude 1,5-dioxacyclohexadecane-6,16-dione is 79%, based on the amount of polyester used. The product is purified by recrystallization from methanol. The pure product has a melting point of 46° C.

EXAMPLES 3-6

Example 2 was repeated, varying the quantity and nature of the organotin component of the catalyst, as shown in Table 1 wherein the yields are also listed.

TABLE 1

| Example | Organotin Compound | Amount Employed | Crude Yield |
|---|---|---|---|
| 3 | Dioctyltin oxide | 1.5 g | 68% |
| 4 | Diphenyltin oxide | 3 g | 71% |
| 5 | Dilauryltin oxide | 3 g | 65% |
| 6 | Diphenyltin oxide | 1.5 g | 67% |

EXAMPLE 7

100 g of a polyester of undecanedioic acid and 1,4-butanediol, having a degree of polymerization of 33 and an acid number of 5 mg KOH/g, is thoroughly mixed with 3 g of di-octyltin oxide and 3 g of O,O-dioctadecyl-(3,5-di-tert-butyl-4-hydroxybenzyl)-phosphonate in a distillation flask of a conventional vacuum distillation apparatus. The reaction mixture is thermolyzed for 5 hours under vacuum (pressure: 0.1 mbar) and at a temperature of 270° C. The crude yield of 1,6-dioxacycloheptadecane-6,17-dione is 72%, based on the amount of polyester employed. Purification is accomplished by distillation under vacuum. Yield of pure product: 67%, boiling point$_{0.01\ mbar}$ = 146°-148° C.

EXAMPLE 8

100 g of a polyester of undecanedioic acid and 2,2-dimethyl-1,3-propanediol, having a degree of polymerization of 26 and an acid number of 7 mg KOH/g, is thoroughly mixed with 3 g of dioctyltin oxide and 3 g of O,O-dioctadecyl-(3,5-di-tert-butyl-4-hydroxybenzyl)-phosphonate in a distillation flask of a conventional vacuum distillation apparatus. The reaction mixture is thermolyzed for 6 hours under vacuum (pressure: 0.15 mbar) and at a temperature of 270° C. The yield of crude 1,5-dioxa-3,3-dimethylcyclohexadecane-6,16-dione is 61%, based on the amount of polyester employed. The crude product is recrystallized from methanol. The pure product has a melting point of 64° C.

EXAMPLES 9-18 (Comparative Examples)

100 g of a polyester of undecanedioic acid and 1,3-propanediol, having a degree of polymerization of 29 and an acid number of 7 mg KOH/g, is mixed with 3 g of one of the catalysts listed in Table 2 (derived from French Pat. No. 796,410) in a distillation flask of a conventional vacuum distillation apparatus. The mixture is thermolyzed for 4-5 hours under vacuum (pressure: less than 0.5 mbar) at 270° C. The yields of crude 1,5-dioxacyclohexadecane-6,16-dione, based on the amount of polyester employed, are listed in Table 2.

TABLE 2

| Example | Catalyst | Crude Yield |
|---|---|---|
| 9 | $SnCl_2 \cdot 2 H_2O$ | 14% |
| 10 | $MnCl_2 \cdot 4 H_2O$ | 8% |
| 11 | $FeCl_2 \cdot 4 H_2O$ | 9% |
| 12 | $MgCl_2 \cdot 6 H_2O$ | 3% |
| 13 | $CoCl_2 \cdot 6 H_2O$ | 10% |
| 14 | $Co(NO_3)_2 \cdot 6 H_2O$ | 8% |
| 15 | $MnCO_3$ | 7% |
| 16 | MgO | 2% |
| 17 | $MgCO_3$ | 14% |
| 18 | Mg Powder | 3% |

EXAMPLE 19 (Comp. Example)

Example 2 was repeated, using 3 g of $PbO_2$ as the catalyst. The crude yield of 1,5-dioxacyclohexadecane-6,16-dione is 56%, based on the amount of polyester employed. The crude product contains 380 mg of lead per kilogram.

EXAMPLE 20 (Comparative Example)

Example 2 was repeated, using 3 g of $Pb(NO_3)_2$ as the catalyst. The crude yield of 1,5-dioxacyclohexane-6,16-dione is 68%, based on the amount of polyester employed. The crude product contains 450 mg of lead per kilogram.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of cyclic esters of undecanedioic acid with aliphatic diols which comprises thermolyzing the corresponding linear polyesters derived from said acid and said diols, under reduced pressure at temperatures of 200°-300° C. in the presence of organotin and phosphonate catalysts wherein the organotin catalysts are of the formula

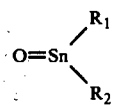

wherein $R_1$ and $R_2$ are alkyl of 1-18 carbon atoms of aryl or aralkyl each of 6-36 carbon atoms, and the phosphonate is O,O-dialkyl-(3,5-di-tert-butyl-4-hydroxybenzyl)-phosphonate, the alkyl groups of which each contain 2-18 carbon atoms.

2. The process of claim 1, wherein the aliphatic diols are those having 2-12 carbon atoms or derivatives thereof having 1 or 2 alkyl substituents each having 1-4 carbon atoms.

3. The process of claim 1, wherein the organotin compound and the O,O-dialkyl-(3,5-di-tert-butyl-4-hydroxybenzyl)-phosphonate each is employed in amounts of 0.1–5% by weight based on the amount of polyester employed.

4. The process of claim 3, wherein the organotin compound and the O,O-dialkyl-(3,5-di-tert-butyl-4-hydroxybenzyl)-phosphonate each is employed in amounts of 1–3% by weight based on the amount of polyester employed.

5. The process of claim 1, wherein the phosphonate catalyst is O,O-octadecyl-(3,5-di-tert-butyl-4-hydroxybenzyl)-phosphonate.

6. The process of claim 1, wherein the organotin catalyst is dipropyltin oxide, dibutyltin oxide, dihexyltin oxide, dioctyltin oxide, didodecyltin oxide, dipentadecyltin oxide, dioctadecyltin oxide, diphenyltin oxide, or dibenzyltin oxide.

7. The process of claim 6, wherein the phosphonate catalyst is O,O-octadecyl-(3,5-di-tert-butyl-4-hydroxybenzyl)-phosphonate.

8. The process of claim 7, wherein the organotin catalyst is dioctyl-, dilauryl-, distearyl-, or diphenyltin oxide.

9. The process of claim 1, wherein the thermolysis is conducted at a temperature of 250°–280° C.

10. The process of claim 9, wherein the pressure is below 1 mbar.

11. The process of claim 1, wherein the pressure is below 5 mbar.

12. The process of claim 2, wherein the aliphatic diols are ethylene glycol, 1,2-propanediol, 1,3-propanediol, 1,4-butanediol, 1,6-hexanediol, 1,12-dodecanediol, 2,2-dimethyl-1,3-propanediol, 3,3-dimethyl-1,5-pentanediol, 2,2-diethyl-1,3-propanediol, or 2-n-butyl-2-ethyl-1,3-propanediol.

13. The process of claim 1, wherein the mean degree of polymerization of the polyester is 3–200.

* * * * *